(12) United States Patent
Crivello et al.

(10) Patent No.: US 6,632,960 B2
(45) Date of Patent: Oct. 14, 2003

(54) DIARYLIODONIUM SALT CATALYSTS MADE FROM IODOTOLUENE AND A METHOD FOR PREPARING THEM

(75) Inventors: James V. Crivello, Clifton Park, NY (US); Georg Feldmann-Krane, Mulheim (DE); Sascha Oestreich, Essen (DE)

(73) Assignees: Goldschmidt AG, Essen (DE); Polyset Chemical Company Inc., Mechanicville, NY (US)

(*) Notice: Subject to any disclaimer, the term of this patent is extended or adjusted under 35 U.S.C. 154(b) by 0 days.

(21) Appl. No.: 10/177,549

(22) Filed: Jun. 21, 2002

(65) Prior Publication Data

US 2002/0193619 A1 Dec. 19, 2002

(51) Int. Cl.$^7$ ............................................. C07C 309/00
(52) U.S. Cl. ........................ 562/30; 562/30; 562/113; 568/1; 568/9
(58) Field of Search .................. 568/9, 1, 579, 568/584–585; 556/64, 1; 562/30, 113

(56) References Cited

U.S. PATENT DOCUMENTS

| 4,683,317 | A | | 7/1987 | Crivello et al. ............... 556/64 |
|---|---|---|---|---|
| 5,073,643 | A | | 12/1991 | Crivello ........................ 556/64 |
| 5,079,378 | A | | 1/1992 | Crivello ........................ 556/64 |
| 5,426,222 | A | * | 6/1995 | Wargo et al. ................ 562/602 |

FOREIGN PATENT DOCUMENTS

| EP | 1088813 A2 | 4/2001 | ......... C07C/271/12 |

OTHER PUBLICATIONS

CA:131:136806 abs of EP 933681 Aug. 4, 1999.*
CA:134:115995 abs of Tetrahedron Letters by Ren et al 41(45) pp 8669–8672 2000.*

* cited by examiner

Primary Examiner—Jean F. Vollano
(74) Attorney, Agent, or Firm—Heslin Rothenberg Farley & Mesiti P.C.; Martha L. Boden, Esq.

(57) ABSTRACT

Diaryliodonium salts are disclosed, as well as a method for preparing them, in which one of the aryl groups bonded to the positively-charged iodine ion contains a methyl substituent, and the other one contains a hydroxyl-substituted alkoxy group. The salts are synthesized from (o, m, or p)-iodotoluene, as opposed to iodobenzene, and therefore do not pose a carcinogenic risk. In addition, the present salts are unexpectedly more soluble in most organic solvents, as well as in nonpolar monomers, than the corresponding benzene catalysts. The salts are useful as cationic photoinitiators, cationic thermal initiators (often combined with a cocatalyst, e.g. copper), and as starting materials in the synthesis of urethane-containing iodonium salts.

23 Claims, No Drawings

DIARYLIODONIUM SALT CATALYSTS MADE FROM IODOTOLUENE AND A METHOD FOR PREPARING THEM

FIELD OF THE INVENTION

The present invention relates generally to catalysts used in cationic polymerizations, and more particularly to diaryliodonium salt photo/thermal initiators, and a method for preparing them, wherein one of the aryl groups attached to the iodine moiety is substituted with a methyl group, and the other is substituted with an alkoxy group having a hydroxy group therein.

BACKGROUND OF THE INVENTION

Photoinitiated cationic polymerization is a rapid, energy efficient and pollution-free method for curing cationically polymerizable monomers, such as epoxy monomers. Particularly efficient photoinitiators include onium salts, such as diaryliodonium (1) salts:

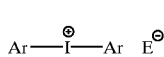

(1)

E⁻ is typically [BF₄]⁻, [PF₆]⁻, [AsF₆]⁻, or [SbF₆]⁻.

Within the industry, diaryliodonium, as well as triarylsulfonium salts, have been the principal photoinitiators for cationic ultraviolet (UV) curing. Diaryliodonium salts having the structure shown in (1) have been described in the patent literature, notably in U.S. Pat. No. 4,683,317 to the instant inventor, J. V. Crivello, and colleague J. L. Lee. Therein, the subject salts are produced from the condensation of aryliodosotosylates and aryl ketones. The salts have been used as photoinitiators to effect deep section UV cures in photopolymerizable organic materials used for the encapsulation of electronic components.

J. V. Crivello also disclosed in U.S. Pat. No. 5,079,378 that the organic solubility of diaryliodonium salts could be increased by substituting at least one aryl radical with a long chain ester. In addition, J. V. Crivello reported in U.S. Pat. No. 5,073,643 hydroxyl-bearing diaryliodonium salts, wherein at least one aryl group is substituted with a long chain alkoxy group having a hydroxyl moiety attached at the 2-position of the alkoxy group. These salts were prepared by reacting a monoaryloxy-2-hydroxyalkane with [hydroxy(tosyloxy)iodo]benzene. The iodonium salts discussed in the aforementioned patents may also be used in thermally curable systems with or without a copper cocatalyst. An example of such a salt is [4-(2-hydroxy-1-tetradecyloxy)-phenyl] phenyliodonium hexafluoroantimonate, (commercially available from Polyset Corporation as PCX 2506 or from Sartomer as CD-1012), which is represented by the following structure (2):

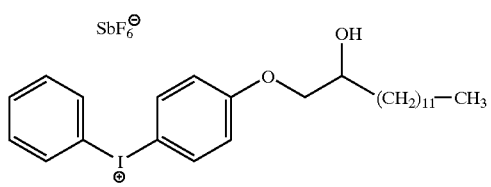

(2)

EP 1088813 A2 discloses other modified diaryliodonium salts, which are reported to exhibit improved solubility in nonpolar media including organopolysiloxanes containing epoxy groups and n-alkanes. The salts contain a urethane moiety and are prepared by reacting hydroxyl-containing iodonium salts, such as the one depicted above, with reagents containing isocyanate groups. The reduced tendency of the resulting urethanes to crystallize makes them more soluble in nonpolar media, e.g., alkanes or siloxanes, than the hydroxyl-containing iodonium salt starting materials.

One disadvantage in using the aforementioned diaryliodonium salts is that often, benzene is produced when these catalysts are used in UV curing. Thus, benzene has the potential to vaporize or leach out of the polymer film. Because benzene is carcinogenic, the use of materials that may yield benzene is becoming more and more restricted. Therefore, it is desirable to find photo/thermal initiators which do not have this drawback, but which retain the solubility advantages associated with known onium salts.

A need, therefore, exists for catalytic onium salts, as well as a method of preparing them, wherein benzene is not a potential by-product when the photo/thermal intiatiors are employed for curing purposes. However, the solubility of such salts should not be compromised when compared with benzene-containing salts.

The present invention fulfills this need by providing hydroxyl-bearing iodonium salts, which do not contain benzene, and a method for preparing them from monoaryloxy-2-hydroxyalkanes and [hydroxy(tosyloxy)] iodoaryl salts. These hydroxyl-bearing iodonium salts are useful as photo/thermal initiators in cationic polymerization reactions, as well as for use in preparing the aforementioned urethanes. The present catalytic salts are also surprisingly more soluble than their benzene counterparts.

SUMMARY OF THE INVENTION

The present invention is directed to diaryliodonium salts and a method for preparing them in which one of the aryl groups bonded to the positively-charged iodine ion contains a methyl substituent, and the other one contains a hydroxyl-substituted alkoxy group. These salts are extremely useful as cationic photoinitiators, cationic thermal initiators, and as starting materials in the synthesis of urethane-containing iodonium salts. The present invention eliminates the problem of benzene leaching during polymerization and curing. The salts exhibit unexpectedly improved solubility in most organic solvents, as well as in nonpolar media, as compared with prior art salts prepared from iodobenzene. Another benefit of the present invention is that when the instant diaryliodonium salts contain the hexafluorophosphate anion, i.e., [PF₆]⁻, the salts are surprisingly more soluble in nonpolar media than salts made from iodobenzene, which contain the hexafluoroantimonate anion. This is advantageous because antimony is generally considered to be a toxic metal, and its use is becoming quite limited. The present method also allows for preparation of the salts in good to excellent yield.

Briefly, in one aspect, the present invention includes diaryliodonium salts having the general formula (I)

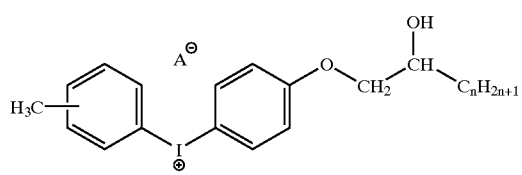

(I)

wherein n is 0 or an integer from 1 to 25. The methyl substituent may be located at any position of the aryl ring, i.e., at the 2, 3, or 4-carbon relative to the carbon attached to the iodine atom, which is identified as the 1-carbon. The 2-, 3-, and 4-carbon positions are also known as ortho-, meta-, and para-, respectively, which may also be represented herein as o-, m-, and p-, respectively, as anyone of ordinary skill would know. $A^-$ is the anion of a complex metal halide or of a strong protonic acid. Anions, $A^-$, derived from complex metal halide salts may be represented as $[MX_m]^-$, wherein M is boron, gallium, phosphorus, or antimony; X is halogen, and the value of m is 4 or 6. Alternatively, X may be $C_6F_5$ when M is boron or gallium, and m is 4. Examples of such ions include $[BF_4]^-$, $[PF_6]^-$, $[AsF_6]^-$, $[SbF_6]^-$, $[B(C_6F_5)_4]^-$, and $[Ga(C_6F_5)_4]^-$. Anions from strong protonic acids include, e.g., $[ClO_4]^-$, $[CF_3SO_3]^-$, $[FSO_3]^-$, $[CH_3SO_3]^-$, and $[C_4F_9SO_3]^-$. It should be noted that a negatively charged moiety is conventionally indicated herein by a minus sign, either in a circle or without the circle. Each symbol is used interchangeably, and may be positioned as a superscript relative to the moiety. Similarly, a positively charged moiety is denoted by a plus symbol, with or without the circle.

In another aspect, the present invention provides a method for preparing an iodonium salt having the general formula (I) above. The method comprises reacting a compound having formula (II):

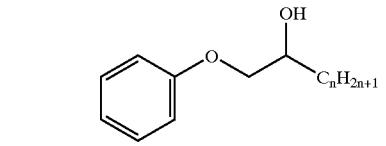

(II)

with a [hydroxy(tosyloxy)]iodoaryl salt (III) in the presence of a suitable solvent and a reagent providing the anion, $A^-$. Structure (III) is represented as:

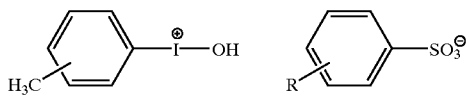

(III)

The substituent, R, is methyl ($CH_3$) or hydrogen (H).

In yet another aspect, the present invention is a method for preparing a diaryliodonium salt in which one aryl group is substituted with a long chain alkoxy group possessing a hydroxyl moiety in the 2-position, and the other aryl group is substituted with a methyl group. The method comprises reacting a monoaryloxy-2-hydroxyalkane with a [hydroxy (tosyloxy)]iodoaryl salt of structure (III) above in the presence of a suitable solvent and providing an anion from a complex metal halide or a strong protonic acid, such as the anions mentioned above.

DESCRIPTION OF THE PREFERRED EMBODIMENTS

A general scheme for the synthesis of the diaryliodium salts of this invention is as follows:

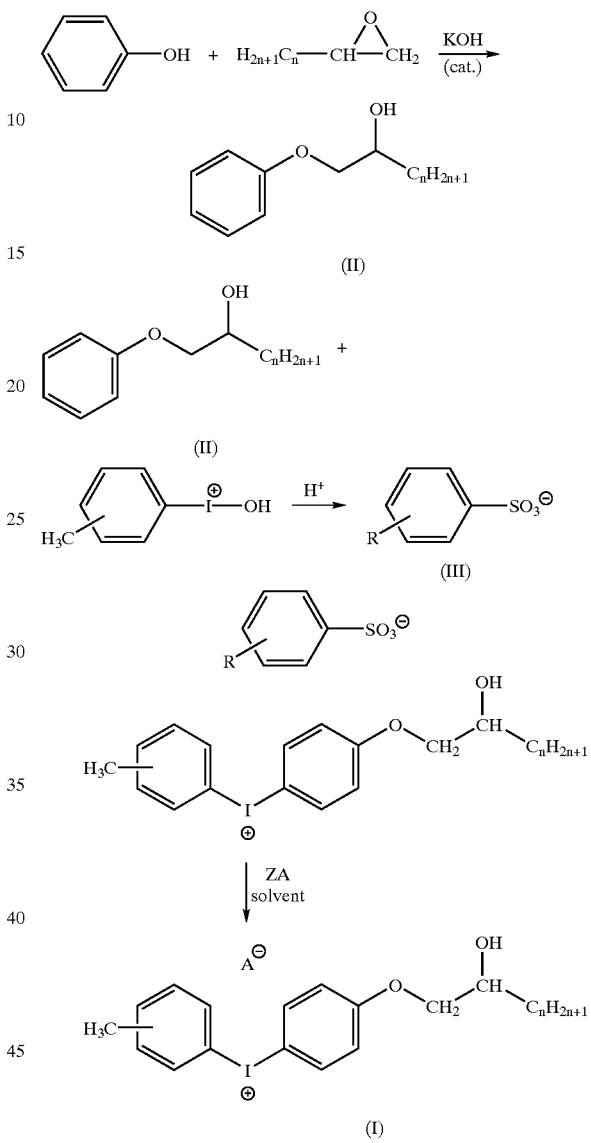

The above scheme is a general synthesis which can be expanded to cover a large family of such catalysts. As mentioned above, the methyl group may be located at the otho-, meta-, or para-position of the aryl ring. More specifically, when the substituent, —$CH_3$, is attached to the carbon atom adjoining the iodine carbon, it is located in the ortho-position (also referred to as the 1,2 position-); when methyl is on the third carbon, it is located in the meta-position (1,3-); and when it is located on the carbon opposite the iodine carbon, it is in the para-position (1,4-). For convenience and economic reasons, methyl is typically located in para-position.

Briefly, to prepare iodonium salts of formula (I), wherein the value of n is 0, or an integer from 1 to 25, a monoaryloxy-2-hydroxyalkane having formula (II) above is reacted with a [hydroxy(tosyloxy)]iodoaryl salt (structure (III), wherein R is methyl or hydrogen) in the presence of a suitable solvent and a reagent source, ZA, which provides anion A⁻. Suitable solvents for the reaction include those which will solubilize the complex metal halide salt or the strong protonic acid. Examples include, but are not limited to, acetone, methyl ethyl ketone, ethanol, methanol, or water.

Compound (II) is prepared by reacting phenol with a 1,2-epoxyalkane. The [hydroxy(tosyloxy)]iodoaryl salt (III) is prepared by the reaction of (o, m, or p)-iodotoluene with an oxidizing agent, such as peracetic acid, m-chloroperbenzoic acid, potassium iodate, or potassium persulfate, the product of which is then reacted with either benzenesulfonic acid or one of the isomers of toluenesulfonic acid. The isomers of iodotoluene are available from a variety of commercial sources, including Aldrich and Flurochem USA. As mentioned above, p-iodotoluene will often be the most readily used because of its cost. The other reagents used in the reaction are also readily available from commercial sources.

Anion A⁻ may be an anion of a complex metal halide, represented generally as $[MX_m]^-$, wherein M is a metal, such as boron, gallium, arsenic, phosphorus, and antimony; m is 4 or 6, and X is halogen. Examples include, but are not limited to, $[BF_4]^-$, $[PF_6]^-$, $[AsF_6]^-$, and $[SbF_6]^-$. Alternatively, X may be $C_6F_5$ when M is boron or gallium, and m is 4, i.e., $[B(C_6F_5)_4]^-$, or $[Ga(C_6F_5)_4]^-$. A⁻ may instead be an anion from a strong protonic acid, e.g., $[ClO_4]^-$, $[CF_3SO_3]^-$, $[FSO_3]^-$, $[CH_3SO_3]^-$, or $[C_4F_9SO_3]^-$. When the anion source reagent is a complex metal halide, then Z, in the above scheme, may be sodium or potassium, for example, and when the anion source is a strong protonic acid, Z is hydrogen.

A major advantage of retaining the hydroxyl group in the iodonium salts (I) used in UV-induced cationic polymerizations, as opposed to forming the urethanes mentioned above, is that during crosslinking, the hydroxyl groups serve as chain transfer agents. This results in a marked acceleration effect on the polymerization rates. The initiator residues become bonded to the matrix of the polymerizing resin, resulting in a decrease in the number of fragments of the initiator which can volatilize or leach out of the polymer film. This factor is of considerable importance for electronic applications in which the photoinitiator is used, since it is known that photoinitiator residues, having ionic character, may degrade electronic performance by interfering with hole/electron transport mechanisms.

Among the many examples of compound (I) is [4-(2-hydroxy-1-tetradecyloxy)-phenyl] 4-methylphenyliodonium hexafluoroantimonate, which is depicted as structure (10):

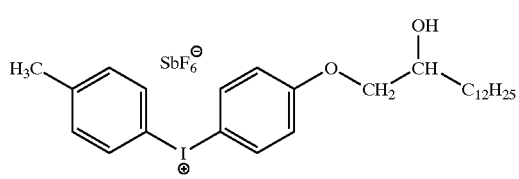

(10)

wherein n is 12, and A⁻ is $SbF_6^-$. Another example is [4-(2-hydroxy-1-tetradecyloxy)-phenyl] 4-methylphenyliodonium hexafluorophosphate (13), wherein n is 12, and A⁻ is $PF_6^-$:

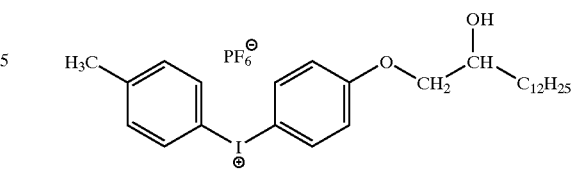

(13)

In these catalysts, as well as the others of the present invention, one of the aryl groups attached to the positively charged iodine atom bears a long chain hydroxyl-substituted alkoxy group, and the other aryl group bears a methyl group substituent. In structures (10) and (13) above, —CH₃ is located in the para-position (4-carbon)of the aryl ring, which is opposite the carbon atom attached to the iodine atom. The above depicted catalysts (10) and (13) are commercially available from Polyset as PCX 2509 and PCX 2519, respectively.

Of additional interest are compounds analogous to structure (I), wherein the methyl group bonded to the aromatic ring is replaced by an alkyl group having from 1 to 6 carbon atoms, such as ethyl, isopropyl, n-propyl, n-butyl, t-butyl, or t-pentyl, for example; by an alkoxy having from 1 to 6 carbon atoms, e.g., methoxy, ethoxy, and the like; or by chloro, bromo, fluoro, or haloalkyl having from 1 to 6 carbon atoms.

It should be noted that diaryliodonium salts containing the hexafluoroantimonate anion, $[SbF_6]^-$, have often been selected as the preferred cationic catalysts due to their excellent organic solubility properties and high reactivity. However, use of these salts is becoming problematic because of toxicity concerns about antimony. Thus, alternative salts having anions other than $[SbF_6]^-$, wherein solubility is not sacrificed, are constantly being sought.

Surprisingly, when the present salts include a hexafluorophosphate anion, i.e. $[PF_6]^-$, the solubility advantages associated with hexafluoroantimonate salts $[SbF_6]^-$ made from iodobenzene are retained, in fact, improved. This is unexpected because, based on previously known catalysts synthesized from iodobenzene, e.g. structure (2) above, hexafluoroantimonate salts were believed to be more soluble than the corresponding hexafluorophosphate salts. By contrast, the present hexafluorophosphate catalysts made from iodotoluene are unexpectedly and significantly more soluble in nonpolar media than even the highly soluble hexafluoroantimonate catalysts made from iodobenzene. For example, the above depicted hexafluorophosphate salt derived from iodotoluene (13) (Polyset PCX-2519) dissolved to a 3 wt. % solution at 70° C. in moderately nonpolar 3,4-epoxycyclohexylmethyl 3',4'-epoxycyclohexanecarboxylate (EECH)(Union Carbide ERL-4221E) in 2.5 hours versus 4.5 hours for the benzene hexafluoroantimonate (2)(Polyset, PCX-2506). In addition, catalyst (13) (PCX-2519) dissolved to a 3 wt % solution at 70° C. in nonpolar 1,1,3,3-tetramethyl-1,3-bis[2-(7-oxabicyclo[4.1.0]hept-3-yl)ethyl] disiloxane (Polyset PC1000) in 30 minutes versus 2.25 hours for the benzene hexafluoroantimonate. The hexafluorophosphate salts of the present invention have the additional advantage of avoiding the toxicity concerns that inevitably arise in using the antimonate-derived photo/thermal initiator.

Furthermore, the iodotoluene-based hexafluorophosphate salts of the present invention are also surprisingly and significantly more soluble in nonpolar media than the corresponding hexafluorophosphate salts made from iodobenzene, as indicated in the following Table:

TABLE

Iodonium Catalyst Solubility Studies @ 70° C.

| | Formulation A (parts by weight) | Formulation B (parts by weight) |
|---|---|---|
| COMPARISON 1 | | |
| Vikolox 7190 (Epoxidized Linseed Oil) | 100 | 100 |
| (PCX-2508) | 3 | — |
| (Iodonium Hexafluorophosphate based on Iodobenzene) | | |
| Structure (13) PCX-2519 | — | 3 |
| (Iodonium Hexafluorophosphate based on Iodotoluene) | | |
| Time @ 70° C. (for clear solution) | 4 ½ hrs. | 3 hrs. |
| Solution Stability (after 7 days @ 25° C.) | Stable & Clear | Stable & Clear |
| COMPARISON 2 | | |
| PC-1000 (Epoxy Siloxane Monomer) | 100 | 100 |
| Structure (PCX-2508) | 3 | — |
| Structure (13)(PCX-2519) | — | 3 |
| Time @ 70° C. (for clear solution) | 2 ½ hrs. | ½ hr. |
| Solution Stability (after 7 days @ 25° C.) | Stable & Clear | Stable & Clear |
| COMPARISON 3 | | |
| ERL 4221E (Cycloaliphatic Epoxy Resin) | 60 | 60 |
| Structure (PCX-2508) | 40 | — |
| Structure (13)(PCX-2519) | — | 40 |
| Time @ 70° C. | 2 hrs. | 1 hr. |
| Solution Stability (after 7 days @ 25° C.) | Clear, but trace of precipitation | Stable & Clear |
| Solution Stability (after 14 days @ 25° C.) | Fully Precipitated | Stable & Clear |

The above Table compares the solubility of an iodonium hexafluorophosphate salt derived from iodobenzene, wherein n is 12, and the anion is [PF$_6$]$^-$ (structure (2) above except that [SbF$_6$]$^-$ is replaced by [PF$_6$]$^-$) (Polyset PCX-2508) with the solubility of the corresponding iodonium hexafluorophosphate salt derived from iodotoluene (structure 13)(Polyset PCX-2519) in three different media: 1) epoxidized linseed oil (EPLO)(Atochem-Vikolox 7190) (nonpolar); 2) 3,4-epoxycyclohexylmethyl 3',4'-epoxycyclohexanecarboxylate (EECH)(Union Carbide-ERL-4221E) (moderately nonpolar); and 3) 1,1,3,3-tetramethyl-1,3-bis[2-(7-oxabicyclo[4.1.0]hept-3-yl)ethyl] disiloxane (Polyset-PC1000) (nonpolar).

In the Table, Comparison 1 shows that the iodotoluene hexafluorophosphate salt (13) (PCX-2519) dissolved in EPLO in three hours to form a 2.9 wt. % (3 parts by weight) solution at 70° C., whereas the iodobenzene hexafluorophosphate salt (Polyset PCX-2508) dissolved in four hours. Comparison 2 indicates that the iodotoluene hexafluorophosphate salt (13)(PCX-2519) dissolved in Polyset PC1000 to form a 2.9 wt. % (3 parts by weight) solution at 70° C. in half an hour versus two and a half hours for the iodobenzene hexafluorophosphate salt (Polyset PCX-2508). Finally, in ERL-4221E, the iodotoluene hexafluorophosphate salt (13) (PCX-2519) dissolved to form a 40 wt % solution at 70° C. in one hour versus two hours for the iodobenzene hexafluorophosphate salt (Comparison 3).

Furthermore, as shown in the Table, the catalyst solutions containing the present iodotoluene salts are much more stable with time than the corresponding solutions containing the iodobenzene salts. For instance, Comparison 3 shows that after 7 days at 25° C., the iodobenzene hexafluorophosphate catalyst began to precipitate, and after 14 days, it had fully precipitated out of solution. By contrast, the solution containing the iodotoluene catalyst remained stable and clear, a significant improvement. The solution stability of a photo/thermal initiator is important since, in many cases, these materials are either commercialized in solutions or dissolved by the final end user.

The iodonium salt catalysts of the present invention are useful for carrying out photoinitiated polymerization of cationically polymerizable monomers including: mono, di and polyfunctional epoxides, e.g., bisphenol-A diglycidyl ether; butanediol diglycidyl ether, 3,4-epoxycyclohexyl-3', 4'-epoxycyclohexane carboxylate, phenol novolac epoxides, poly(1,2-butadiene oxide), epoxidized soybean oil, epoxidized linseed oil; vinyl ethers, e.g., diethyleneglycol divinyl ether, triethyleneglycol divinyl ether, dicyclohexanedioldivinyl ether, 1,4-butanediol divinyl ether; vinyl hydrocarbon monomers, e.g., styrene, c-methyl styrene, divinyl benzene, 1,3-diisopropenylbenzene, N-vinyl carbazole, and acenaphthalene. Heterocyclic monomers such as oxetane, trioxane, 1,3-dioxolane, and tetrahydrofuran can also be polymerized using these photoinitiators. One useful application of these photoinitiators is with formulations intended for use as UV curable coatings, e.g., epoxy silicone release coatings, and fiber optic coatings, adhesives and sealants. The photoinitiators can also be used for photoimaging purposes, such as in the fabrication of photoresists for electrical and electronic applications.

In addition, the same diaryliodonium salt catalysts are useful as thermal initiators, with or without copper cocatalysts or free radical initiators. The resulting polymers are useful in a wide variety of applications including molding, pulltrusion, composites, encapsulants, adhesives and foams.

Also, the hydroxyl-containing iodonium salts of the present invention may be combined with reagents containing isocyanates to form urethane-containing iodonium salts, as described in the aforementioned EP 1088813 A2. The resulting urethane photoinitiators exhibit excellent solubility in nonpolar, organic resins.

It should be noted that the following example is included for illustrative purposes only, and that the invention is in no way limited to the embodiment used in the example. In addition, the reactants and reagents used in the reactions described herein are readily available materials. Such materials can be conveniently prepared in accordance with conventional preparatory procedures or obtained from commercial sources.

EXAMPLE 1

Preparation of 1-Phenoxy-2-hydroxytetradecane (8)

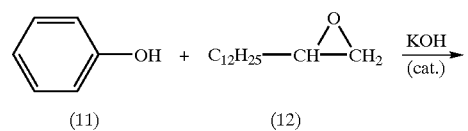

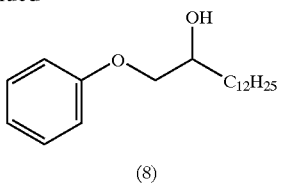

(8)

Combined in a 100 mL round bottomed flask fitted with a magnetic stirrer, thermometer, and reflux condenser, were 31.2 g (0.2 mol) of 1,2-epoxytetradecane (12), 20 g (0.21 mol) of phenol (11) and 0.5 g KOH, as a catalyst. The reaction flask was slowly stirred and heated over the course of one hour to 170° C. After maintaining the reaction flask at this temperature for an additional hour, the reaction mixture was cooled and transferred to a separatory funnel, diluted with ether and extracted with aqueous KOH. The ether was removed on a rotary evaporator leaving a pale yellow oil which, on cooling, rapidly crystallized. The yield of 1-phenoxy-2-hydroxytetradecane (8) was 50.6 g.

Preparation of Hydroxy(tosyloxy)iodotoluene (7)

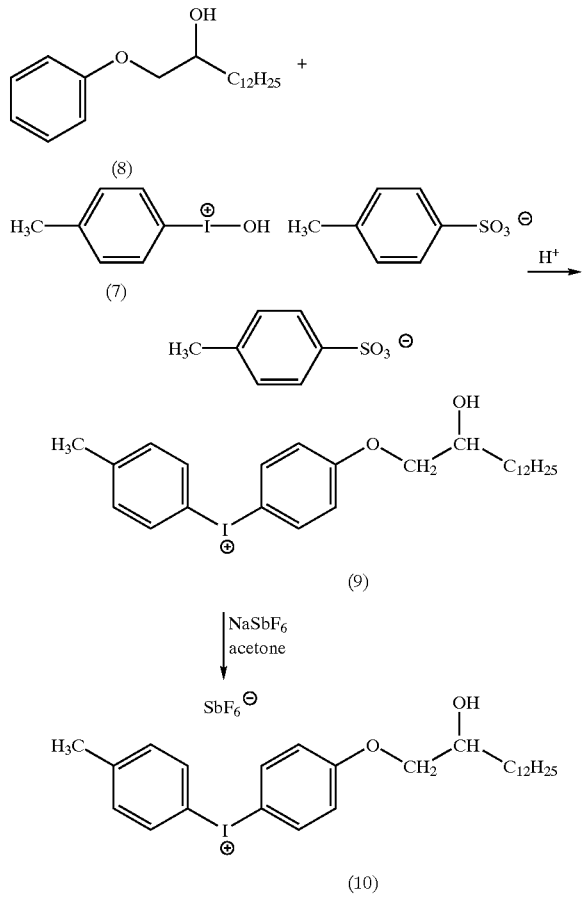

Into a 2000 mL three necked round bottom flask fitted with a condenser, an overhead paddle stirrer and a 1000 mL addition funnel were placed 312 g (1.43 mol.) of iodotoluene (3) (Organica Chemical Co.). The reaction vessel was fitted with a bath that could be alternately heated or cooled. The reaction mixture was heated to 40° C., and 744 g of 35% peracetic acid (4) (FMC Corporation) was added dropwise to the iodotoluene (3) via the addition funnel. The addition required 1 hour and 45 minutes. During the addition, the reaction mixture was maintained at 40–45° C. using a cooling bath. After the addition of peracetic acid (4) was complete, the resulting mixture was stirred for 30 minutes at 35° C. and at the end of that time, 427 g of p-toluenesulfonic acid (6) (Manroe Performance Chemicals) was added rapidly. The product crystallized immediately and was broken up with a spatula. The reaction mixture was stirred for an additional 45 minutes at room temperature.

The reaction was terminated and stored overnight in a freezer. Then, the product was poured into a 14 inch basket centrifuge operating at 2400 rpm to collect the product. The product was washed in the centrifuge with 1000 mL distilled water and was spun for 1 hr to dry the product. The yield of hydroxy(tosyloxy)iodotoluene (7) was 453 g (80.1%).

Preparation of (4-(2-hydroxy-1-tetradecyloxyphenyl))(4-methylphenyl)iodonium Hexafluoroantimonate (10)

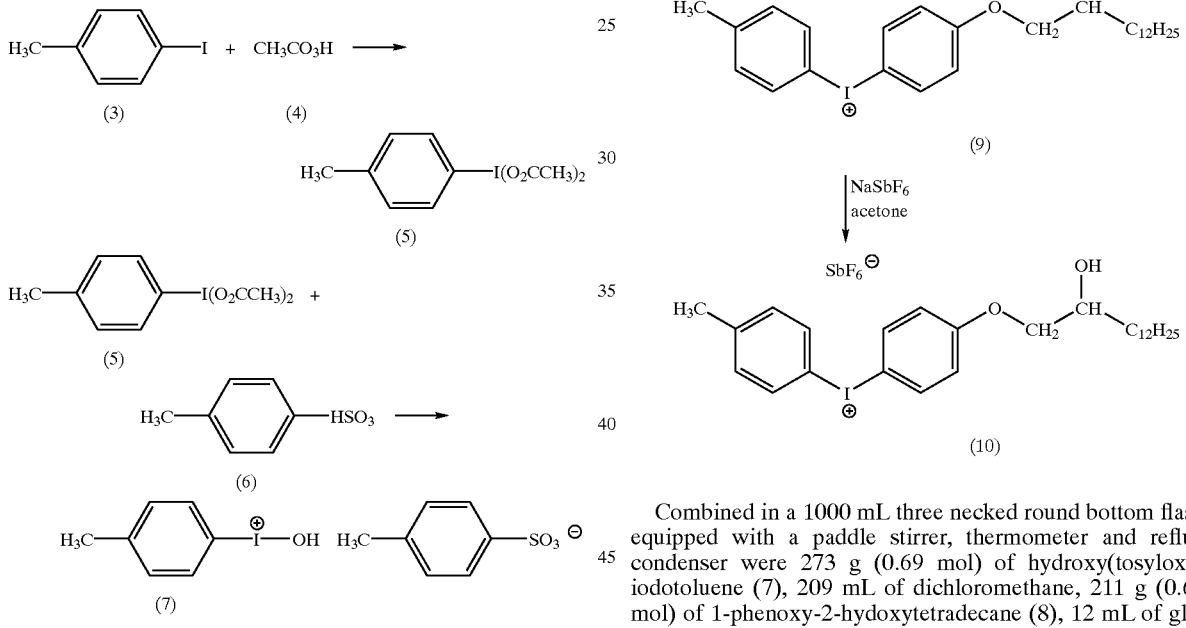

Combined in a 1000 mL three necked round bottom flask equipped with a paddle stirrer, thermometer and reflux condenser were 273 g (0.69 mol) of hydroxy(tosyloxy) iodotoluene (7), 209 mL of dichloromethane, 211 g (0.69 mol) of 1-phenoxy-2-hydoxytetradecane (8), 12 mL of glacial acetic acid and 13 g of p-toluenesulfonic acid (6). The reaction mixture was heated to reflux (40° C.–45° C.) and held within this temperature range for 1 hour and 45 minutes. The red reaction mixture was cooled to 40° C. and 200 mL of acetone was added followed by 270 g of sodium hexafluoroantimonate. An additional 200 mL of acetone was added and the reaction continued stirring for 1 hour.

Next, the reaction mixture was poured into 1500 mL of deionized water and mixed using a paddle stirrer. After 1 hour, the mixture was allowed to settle and the water layer was drawn off the oil layer and discarded. This procedure was repeated one more time and to the resulting viscous oil product 500 g dichloromethane was added. The mixture was stored in a freezer overnight to permit crystallization and the product recovered using a 14 inch basket centrifuge. The product was washed with dichloromethane until the washings were colorless. Then the product was spun (approximately 1 hour) until dry. There were obtained 265 g (50.5% yield) of (4-(2-hydroxy-1-tetradecyloxyphenyl))(4-methylphenyl)iodonium hexafluoroantimonate (10) as a colorless, crystalline compound. This corresponds to formula (I), wherein n is 12, and A⁻ is SbF₆⁻. The melting point of the compound was about 88° C. (average).

EXAMPLE 2

The procedure of Example 1 was followed except that potassium hexafluorophosphate was substituted for sodium hexafluoroantimonate. The resulting product was (4-(2-hydroxy-1-tetradecyloxyphenyl))(4-methylphenyl) iodonium hexafluorophosphate (13), wherein n is 12, and A⁻ is PF₆⁻ in structure (I). The yield was 38%, and the melting point was about 76° C.

DEFINITIONS

"Alkyl", as used herein, refers to saturated hydrocarbon residues containing twenty five or fewer carbons in straight or branched chains, as well as cyclic structures, such as methyl, ethyl, isopropyl, n-propyl, n-butyl, t-butyl, or t-pentyl, and the like. "Alkoxy" refers to the same residues, containing, in addition, an oxygen atom at the point of attachment, e.g., methoxy, ethoxy, and the like. "Aryl" refers to 6-membered aromatic rings such as phenyl, substituted phenyl, naphthyl and the like. "Halogen" means fluorine, chlorine, bromine, or iodine. "Haloalkyl" means an alkyl residue substituted with one or more halogen atoms, e.g., chloromethyl, 3-chloropropyl, 3,4-dichlorophenyl, dichloromethyl, trichloromethyl, fluoromethyl, difluoromethyl. "Alkane" refers to a compound containing an alkyl chain.

All of the patents and patent applications mentioned above are incorporated herein by reference.

While the invention has been particularly shown and described with reference to preferred embodiment(s) thereof, it will be understood by those skilled in the art that various changes in form and details may be made therein without departing from the spirit and scope of the invention.

What is claimed is:

1. A method for preparing a diaryliodonium salt having the formula (I):

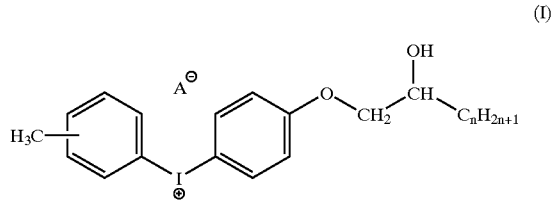

wherein n is 0 or an integer from 1 to 25; and

A⁻ is an anion of a strong protonic acid or of a complex metal halide, wherein said complex metal halide anion is represented by the formula

[MX$_m$]

wherein m is 4 or 6;

M is selected from the group consisting of boron, phosphorus, gallium, arsenic, and antimony; and X is halogen or $C_6F_5$, wherein when X is $C_6F_5$, then M is boron or gallium, and m is 4;

wherein said method comprises reacting a compound of formula (II):

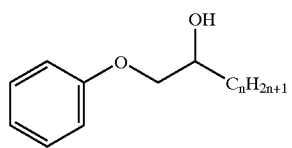

with an [hydroxy(tosyloxy)]iodoaryl salt of structure (III)

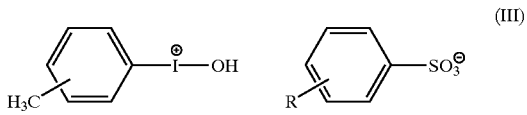

wherein R is methyl or hydrogen, and wherein said reacting step is conducted in the presence of a suitable solvent and a reagent providing said anion.

2. The method of claim 1, wherein said anion A⁻ is selected from the group consisting of [BF₄]⁻, [PF₆]⁻, [AsF₆]⁻, [SbF₆]⁻, [B(C₆F₅)₄]⁻, [Ga(C₆F₅)₄]⁻, [ClO₄]⁻, [CF₃SO₃]⁻, [FSO₃]⁻, [CH₃SO₃]⁻, and [C₄F₉SO₃]⁻.

3. The method of claim 2, wherein said anion A⁻ is [SbF₆]⁻.

4. The method of claim 2, wherein said anion A⁻ is [PF₆]⁻.

5. The method of claim 2, wherein the methyl substituent, —CH₃, of said structures (I) and (III) is located in the para-position of the aryl ring relative to the iodine atom.

6. The method of claim 2, wherein n is 12.

7. The method of claim 6, wherein said anion A⁻ is [SbF₆]⁻.

8. The method of claim 7, wherein the methyl substituent, —CH₃, of said structures (I) and (III) is located in the para-position of the aryl ring relative to the iodine atom.

9. The method of claim 6, wherein said anion A⁻ is [PF₆]⁻.

10. The method of claim 9, wherein the methyl substituent, —CH₃, of said structures (I) and (III) is located in the para-position of the aryl ring relative to the iodine atom.

11. A method for preparing a diaryliodonium salt in which one aryl group is substituted with a long chain alkoxy group possessing a hydroxyl moiety in the 2-position, and the other aryl group is substituted with a methyl group, wherein said method comprises reacting a monoaryloxy-2-hydroxyalkane with an [hydroxy(tosyloxy)]iodoaryl salt in the presence of a suitable solvent and providing an anion from a complex metal halide salt or a strong protonic acid.

12. The method of claim 11, wherein said anion is selected from the group consisting of [BF₄]⁻, [PF₆]⁻, [AsF₆]⁻, [SbF₆]⁻, [B(C₆F₅)₄]⁻, [Ga(C₆F₅)₄]⁻, [ClO₄]⁻, [CF₃SO₃]⁻, [FSO₃]⁻, [CH₃SO₃]⁻, and [C₄F₉SO₃]⁻.

13. A diaryliodonium salt having formula (I):

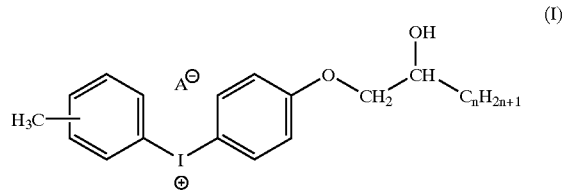

wherein n is 0 or an integer from 1 to 25; and

A⁻ is an anion of a strong protonic acid or of a complex metal halide, wherein said complex metal halide anion is represented by the formula $[MX_m]^{\ominus}$ wherein m is 4 or 6;

M is selected from the group consisting of boron, phosphorus, gallium, arsenic, and antimony; and X is halogen or $C_6F_5$, wherein when X is $C_6F_5$, then M is boron or gallium, and m is 4.

14. The diaryliodonium salt of claim 13, wherein said anion $A^-$ is selected from the group consisting of $[BF_4]^-$, $[PF_6]^-$, $[AsF_6]^-$, $[SbF_6]^-$, $[B(C_6F_5)_4]$, $[ClO_4]^-$, $[CF_3SO_3]^-$, $[FSO_3]^-$, $[CH_3SO_3]^-$, and $[C_4F_9SO_3]^-$.

15. The diaryliodonium salt of claim 14, wherein said anion $A^-$ is $[SbF_6]^-$.

16. The diaryliodonium salt of claim 15, wherein the methyl substituent, —$CH_3$, is located in the para-position of the aryl ring relative to the iodine atom.

17. The diaryliodonium salt of claim 14, wherein said anion $A^-$ is $[PF_6]^-$.

18. The diaryliodonium salt of claim 17, wherein the methyl substituent, —$CH_3$, is located in the para-position of the aryl ring relative to the iodine atom.

19. The diaryliodonium salt of claim 14, wherein n is 12.

20. The diaryliodonium salt of claim 19, wherein said anion $A^-$ is $[SbF_6]^-$.

21. The diaryliodonium salt of claim 20, wherein the methyl substituent, —$CH_3$, is located in the para-position of the aryl ring relative to the iodine atom.

22. The diaryliodonium salt of claim 19, wherein said anion $A^-$ is $[PF_6]^-$.

23. The diaryliodonium salt of claim 22, wherein the methyl substituent, —$CH_3$, is located in the para-position of the aryl ring relative to the iodine atom.

\* \* \* \* \*